United States Patent [19]

Meserole

[11] Patent Number: 4,906,580
[45] Date of Patent: Mar. 6, 1990

[54] SATURATION MONITOR AND PROCESS
[75] Inventor: Frank B. Meserole, Austin, Tex.
[73] Assignee: Radian Corporation, Austin, Tex.
[21] Appl. No.: 301,647
[22] Filed: Jan. 25, 1989
[51] Int. Cl.⁴ ............... G01N 37/00; G01N 21/17; G01N 33/38
[52] U.S. Cl. ........................... 436/56; 436/79; 436/164; 436/179; 436/181; 436/183; 73/61 R
[58] Field of Search ............ 436/56, 55, 79, 164, 436/179, 181, 183, 34; 73/61 R

[56] References Cited

U.S. PATENT DOCUMENTS

| | | | |
|---|---|---|---|
| 3,368,389 | 2/1968 | Barnett | 73/53 |
| 4,226,114 | 10/1980 | Hagedorn | 73/61 R |
| 4,680,271 | 7/1987 | Williams | 436/55 |

OTHER PUBLICATIONS

Automated Dissolution Rate Studies of Capsules and Tablets by Schroeter and Wagner Jour. of Pharm. Sc. (RS 1.J58) Oct, 1962.

*Primary Examiner*—Barry S. Richman
*Assistant Examiner*—Kimberly A. Trautman
*Attorney, Agent, or Firm*—Klauber & Jackson

[57] ABSTRACT

A process for determining the degree of saturation of a solution comprising a solvent and a compound of limited solubility which involves the steps of (1) diluting a feed solution of the compound of limited solubility, (2) passing a sample of the diluted feed solution through a bed of a solid solution of the compound and a tracer in which the tracer is intrinsically incorporated into the crystal structure of the compound, so that the diluted feed solution being tested becomes saturated with the compound by dissolution of a portion of the solid solution in the bed, (3) measuring the concentration of the tracer in the sample after passage through the bed of solid solution, thus measuring the amount of the compound dissolved from the solid solution to saturate the diluted feed solution, and (4) determining the degree of saturation of the compound in the feed solution from the measured values.

7 Claims, 1 Drawing Sheet

SATURATION MONITOR AND PROCESS

FIELD OF THE INVENTION

This application relates to a measuring process and system and is more particularly concerned with a process and system for monitoring the degree of saturation of a solution comprising a solvent and a compound of limited solubility in the solvent, especially the degree of saturation of an aqueous solution of gypsum.

BACKGROUND OF THE INVENTION

Methods and systems for measuring and monitoring solutions are known and involve a wide variety of techniques. For example, Hagedora U.S. Pat. No. 4,226,114 describes a method of analysis which is based upon measurement of change of enthalpy. Williams U.S. Pat. No. 4,680,271 uses continuous differential colorimetric analysis. Both of these systems are based on techniques which require certain physical or chemical changes to take place, are relatively complex and are apparently limited to use in connection with compounds which are highly soluble in the solvent in which they are measured. In the field of compounds of limited solubility in a solvent, especially gypsum (calcium sulfate dihydrate) in water, particularly when several other chemical components are present, it has heretofore been extremely time consuming to measure the degree of saturation or relative saturation of the compound of interest in the solvent. Measuring relative saturation of a desired component of limited solubility is important in industry because, when such a solution becomes supersaturated with respect to a particular component, e.g. in a process in which the solution is evaporated, the component of limited solubility tends to come out of solution and to deposit on surfaces of processing equipment (scaling), which leads to plugging and heat-tranfer losses and eventually to shutdowns, with concurrent loss in operating time. Two possibilities exist for a solution not in equilibrium with respect to a given compound, either the solution is subsaturated or it is supersaturated. The relative saturation is defined as being less than one in the subsaturated case and greater than one when supersaturated.

In the field of gypsum-in-water solutions, encountered for example in certain gas desulfurization processes, wherein the solutions are evaporated, present techniques for determining the degree of saturation of gypsum in such complex aqueous solutions are, as mentioned, extremely time consuming. For example, two approaches presently used to determine the degree of saturation or relative saturation in solutions of this character are 1) complete chemical analysis of the solution followed by use of a computerized computational scheme, or 2) chemical analysis for calcium and sulfate, equilibration with gypsum solids, and a reanalysis after equilibration. Both of these techniques require significant analytical capability and involve from four to eight hours to complete

OBJECTS OF THE INVENTION

It is, accordingly, an object of this invention to provide an improved method and system for monitoring the degree of saturation of a compound of limited solubility in a solvent.

It is a further object of this invention to provide an improved method of the character indicated which may be carried out in a relatively short time.

It is another object of this invention to provide an improved method for monitoring the degree of saturation of gypsum in aqueous solutions.

It is a still further object of this invention to provide a system for monitoring the degree of saturation of a compound of limited solubility in a solvent.

BRIEF SUMMARY OF THE INVENTION

In accordance with the invention, there is provided a process which comprises (1) diluting a feed solution of the compound of limited solubility (compound of interest or the "target" compound) to be tested, (2) passing a sample of the diluted feed solution through a bed of a solid solution of the target compound and a tracer wherein the tracer is intrinsically incorporated into the crystal structure of the target compound, whereby the diluted solution being tested becomes saturated with the target compound by dissolution of a portion of the solid solution (target compound plus tracer) in the bed, (3) measuring the concentration of the tracer in the sample after passage through the bed of solid solution, whereby to measure the amount of target compound dissolved from the solid solution to saturate the diluted feed solution, and (4) determining the degree of saturation of the target compound in the feed solution from the measured values.

BRIEF DESCRIPTION OF THE DRAWINGS

These and related objects and features of the invention will be apparent from the drawings wherein.

DETAILED DESCRIPTION OF THE ILLUSTRATIVE EMBODIMENTS

Figure 1:
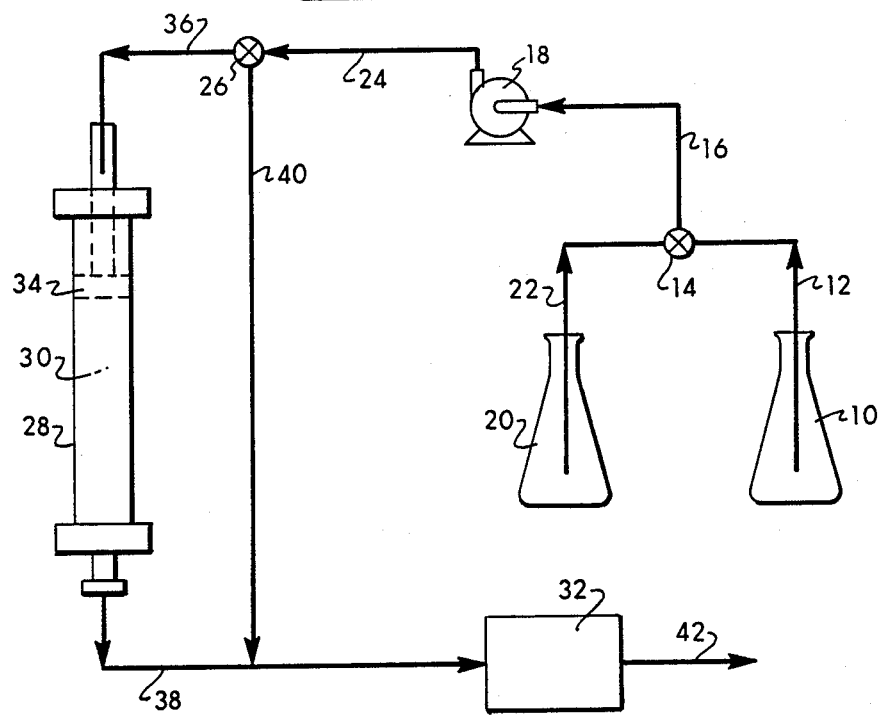
FIG. 1 is a diagrammatic view of a system suitable for carrying out the process of the invention.

Referring to the drawings, and particularly to FIG. 1, there is shown a system which includes a source 10 of the sample in which the relative saturation of compound X in solvent Y is to be tested. The sample is a portion of the feed solution being tested which has been diluted with a predetermined amount of added solvent e.g. water, in the case of a solution of gypsum in water. Sample source 10 is connected by a line 12 to a valve 14 which valve 14 is connected by a line 16 to a pump 18. A source 20 of a saturated solution of compound X in solvent Y is also connected via line 22 to valve 14. Line 24 leads from pump 18 to a second valve 26. Also included, in the system illustrated, is a column 28 for containing a body 30 of the tracer-containing solid solution, and a measuring device or unit 32 which, in the embodiment illustrated, is a flow-through cell of a spectrophotometer. Column 28 is suitably provided at its top with an adjustable plunger 34 effective to reduce the head space produced as the solid solution is gradually dissolved. Second valve 26 is connected to column 28 by a line 36 and column 28 is connected to measuring device 32 by a line 38. A by-pass line 40 connects valve 26 to line 38. The outlet from device 32 is indicated at 42.

Thus, using the system of FIG. 1, a diluted sample of an original (feed) solution being tested is passed from the sample source 10 through the bed 30 of a solid solution of the target compound and a tracer contained in column 28 so that the sample becomes saturated with respect to the target compound accompanied by the tracer. Thereupon, the sample is passed through a device for measuring the concentration of tracer in the sample, and the measured values are used in determining the degree of saturation of the target compound in the original (feed) solution before dilution. The choice of tracer is determined by the ability to measure conveniently the tracer concentration and to form a solid solution with the target compound. For example, if the tracer imparts a color to the solution, as in the case of chromate, a flow-through cell in a spectrophotometer can be used to monitor continuously the tracer concentration in the solution The degree of saturation or relative saturation of the original solution is determined on the basis of the concentration of tracer measured and the level of dilution applied More particularly, the relative saturation monitoring process of this invention can be effectively used to determine the relative saturation of gypsum in solutions directly and rapidly without the need for subsequent analysis of specific components. Thus, in the following discussion, reference will particularly be made to gypsum and to chromate as a tracer for ease of description but, as previously indicated, the process of the invention is applicable to other compounds of limited solubility in a solvent and to other tracers. The process of the invention, as mentioned, employs a tracer technique to measure directly the quantity of gypsum required to saturate a prediluted sample, i.e. a pre-diluted sample of the original solution to be tested. The diluted sample is passed through a bed that is made up of a solid solution of gypsum that has a tracer incorporated into the crystal matrix. In this case, chromate is used as the tracer and deionized water is typically used to effect dilution. The effluent from the bed flows directly into a flow-through cell in a spectrophotometer where the concentration of the dissolved chromate is measured colorimetrically. The quantity of gypsum dissolved is then calculated based on the known quantity of chromate in the solid solution. The amount of chromate that dissolves is directly proportional to the quantity of gypsum that dissolves, since the chromate is bound into the gypsum crystal matrix as a true solid solution.

Conditions of flow rate and exposed surface area are selected such that the solution leaving the column will be saturated with respect to gypsum. The amount of gypsum in the solid solution which dissolves to saturate the diluted test solution will depend upon the solubility of gypsum in that solution and the degree of subsaturation. In general, two or more dilutions of the feed solution are needed to determine the original degree of saturation. On the basis of the foregoing, the degree of saturation can be considered as the reciprocal of the x-axis intercept of a line drawn through the data points which represent the amount of gypsum required to saturate the diluted samples as a function of the dilution value.

In carrying out the process of the invention, a baseline is established by pumping a solution saturated with respect to the target compound e.g. gypsum, from source 20 directly to the measuring unit 32 e.g. a flow-through cell, by-passing the column 28 via line 40. Next, valve 14 is adjusted so that the diluted sample is introduced into line 40 in place of the saturated solution, i.e. still in the column by-pass mode, in order to establish any background absorbance.

In the case of chromate as a tracer, the absorbance is read at 338 nm which is the isobestic point for the chromate, dichromate interconversion due to pH changes in samples. This minimizes the effect of pH on the absorbance, thus reducing the need to control the pH of the samples.

The system is then switched by adjustment of valve 26 to the column mode and the absorbance is again determined, i.e. the sample is caused to flow through bed 30 in column 28. The procedure is repeated with at least two different dilutions of the original solution to be tested. When samples are not being measured the saturated solution in source 20 is pumped through the column 28 to purge out the previous sample and to stabilize the column.

In a particular embodiment, column 28 is 6 mm in diameter. The solid solution 30 is packed into the column 28 to a height of about 20 mm. The adjustable plunger 34 at the top of column 28 will reduce the head space produced as the solid solution is gradually dissolved. The bed 30 of solid solution must be replaced periodically as the solid solution is consumed. Suitably, the column 28 is repacked when approximately one-third of the original quantity of solid solution 30 has dissolved.

In this embodiment, the detector system is a Milton Roy SpectoMonitor 3100 with a low-volume flow-through cell. The cell path length is 1 cm and has a volume of 0.014 mL. Suitably, the output of the monitor is fed to a strip-chart recorder for permanent record.

Ordinarily, the process of the invention is carried out at room temperature, (25° C.). It can, however, be carried out at other temperatures, e.g. 40°-60° C., temperatures which are encountered in gas disulfurization wherein gypsum solutions are formed, by enclosing the sample source and the column 28, for example, in a temperature-controlled oven As will be apparent from the foregoing, an important feature of the invention is the solid solution of the target compound and the tracer. Solid solutions are known and are prepared by techniques appropriate to the compound and tracer involved. In the case of gypsum and a tracer which can be detected colorimetrically, e.g. chromium as chromate, the solid solution is prepared, in accordance with the invention as follows: A solution containing $K_2CrO_4$ and $CaCl_2$ in deionized water is heated to about 50° C and the pH is lowered to 6.5 to 7. A solution of $K_2SO_4$ in hot deionized water is rapidly added to the original solution with vigorous stirring The combined solution and resulting precipitate are stirred, e.g. for an additional 2 hours, with the temperature maintained at about 50° C. The solids are then allowed to settle, the supernatant liquor is decanted, and the wet solids are repeatedly washed with a solution saturated with gypsum, and then dewatered. The solid solution thus obtained contains 2-3% by weight of chromate and is suitably stored in a sealed container for eventual use in the saturation process of the invention The invention will be further understood from the following example of specific application

EXAMPLE

A solid solution of chromium (as chromate) in gypsum is prepared as follows:

There are dissolved 360 g of $K_2CrO_4$ in 1600 ml of deionized water in a 4 L Erlenmeyer flask containing a stir bar for magnetic stirring. Stirring of the solution is begun. There are then dissolved 240 g $CaCl_2.2H_2O$ in 600 mL, and the resulting solution is added to the $K_2CrO_4$ solution. The second solution is allowed to cool to less than 50° C before it is added to the $K_2CrO_4$ solution. The pH of the combined solution is adjusted to between 6.5 and 7.0 with 1M HCl and it is heated to 50° C. There are dissolved 180 g $K_2SO_4$ in 1200 mL of deionized water and the $K_2SO_4$ solution is added to the $CaCl_2/K_2CrO_4$ solution, care being taken that the temperature of the $K_2SO_4$ solution is not greater than 50° C. The combined solution is stirred for about 2 hours, maintaining the temperature between 40°-50° C. Heating and stirring are discontinued and the solids are allowed to settle. The supernatant liquor is decanted and dionized water saturated with gypsum is added to the solids, and thoroughly mixed. The solids are then allowed to settle, and the supernatant liquor is decanted. The addition of water, mixing, settling and decanting are repeated several times until the supernatant liquor shows very little yellow color.

The thus prepared solid solution, which contains gypsum and 2-3 weight percent chromate, is then charged into a column 6 mm in diameter to a height about 20 mm. A baseline is established by feeding a solution saturated with respect to gypsum directly to a flow-through cell (1 cm cell path length; volume 0.014 mL) of a Milton Roy Specto Monitor 3100. The output of the spectrophometer is calibrated by using the solutions of known composition. Thus, a solution of deionized water saturated with gypsum is diluted to give solutions of 90%, 70%, and 50% saturation levels. The amounts of gypsum to resaturate these solutions at 25° C. are 1.54, 4.61, and 7.68 millimoles of gypsum per liter. By measuring these standards, a calibration of the spectrophometer output to the amount of gypsum dissolved is determined and the linearity of the results can be evaluated. Using this calibration curve the amount of gypsum that is dissolved to saturate the samples can be determined.

Figure 2:
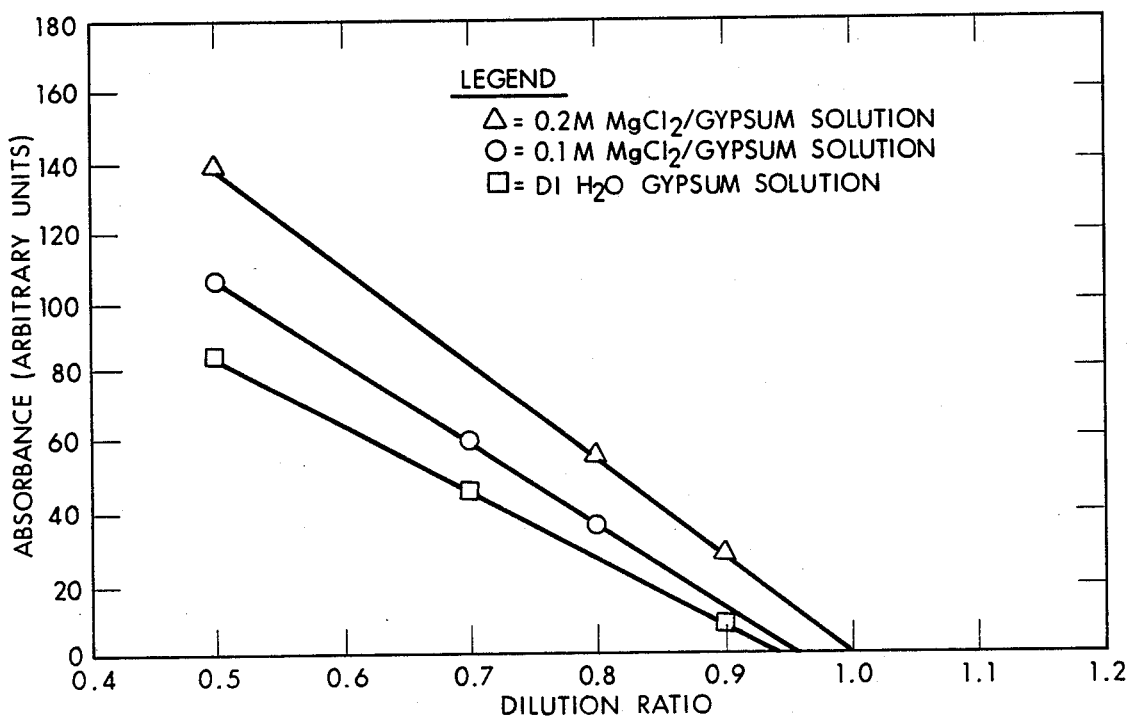
FIG. 2 is a diagram of the plot of illustrative measured points used in detemining relative saturation values in accordance with the invention.

Operating at room temperature (25° C.), a diluted sample to be measured is then prepared by diluting a portion of an aqueous gypsum solution to be tested with deionized water to provide a 0.5 dilution ratio. A portion of the diluted sample is then fed directly to the cell in order to establish background absorbance. The absorbance is read at 338 mm. Next, the diluted sample is then fed through the column containing the solid solution at the rate of 1-2 ml/min. The effluent from the column is passed to the flow-through cell of the Milton Roy Specto Monitor and the quantity of dissolved chromate in the sample measured colorimetrically. Thereupon the column is flushed with a saturated aqueous gypsum solution to purge out the previous sample and to stabilize the column. A second and a third diluted sample to be measured are then prepared by diluting other portions of the aqueous gypsum solution being tested with deionized water to provide 0.7 and 0.9 dilution ratios, respectively, these second and third samples are then passed through the column and into the flowthrough cell exactly as described above in connection with the first diluted sample. In this way the quantity of chromate (and gypsum) dissolved in each sample by passing three different dilutions of the original gypsum solution being tested can be determined. To indicate rapidly the degree of saturation of the undiluted solution, the amount of gypsum dissolved to saturate the diluted samples as determined from the spectrometer measurements is graphed against the dilution ratio. At least two different dilution ratios are needed, for each sample with three, as above, being preferable. The spectrophometer results obtained in this experiment are graphed as a function of the dilution ratio, as seen in FIG. 2. A line is drawn through the data points (squares) and extended to the x-axis. Thus, a curve (or straight line) is drawn through the data that represent the best fit of the values and is extrapolated to the x-axis (zero gypsum dissolved from the solid solution). The dilution ratio value at this intercept represents the dilution of the original sample that would have produced a solution at equilibrium with gypsum. Theoretical calculations of a wide range of solution compositions show that the reciprocal of this dilution ratio is, for practical purposes, the relative saturation of the sample. The reciprocal of the dilution ratio value at the intersection of the extrapolated data-point line and the x-axis gives the desired practical relative saturation value of the original solution from which the samples were prepared In the case of this experiment, the relative saturation value is found to be 1.06. The data points from this experiment are shown in FIG. 2 as squares, as mentioned.

It will be apparent that additional diluted samples can be measured and that other dilutions can be employed. Moreover, when the tracer cannot be measured colorimetrically, other appropriate measuring means can be employed, following the principle of the invention which is based upon saturation of a diluted sample by dissolution of a solid solution of a target compound and a tracer and measuring the resultant amount of tracer (and added target compound) in the sample. The importance of the invention is that it permits the treatment of solutions of compounds, such as gypsum, of limited solubility to determine rapidly their degree of saturation in a practical, (rapid) and non-complex manner. Moreover, while the foregoing example illustrates the measurement of the degree of solubility of gypsum in deionized water, it is a feature of the invention that it permits such determinations of a "target" compound to be made even in the presence of other chemical constituents, such as are found in industrial practice, e.g. in gas desulfuration in the case of gypsum. Thus, as seen in FIG. 2, data points for aqueous solutions of gypsum also containing various concentrations of Mg $Cl_2$ as a contaminant are shown by circles and triangles. $MgCl_2$ is a contaminant known to have a significant effect upon gypsum solubility in water.

It will be obvious that various changes and modifications can be made without departing from the invention as defined in the appended claims and it is intended, therefore, that all matter contained in the foregoing description and in the drawing shall be interpreted as illustrative only and not as limitative of the invention.

I claim:

1. A process for determining the degree of saturation of a solution comprising a solvent and a compound of limited solubility therein, which comprises the steps of (1) diluting a feed solution of the compound of limited solubility, (2) passing a sample of the diluted feed solution through a bed of a solid solution of said compound and a tracer wherein the tracer is intrinsically incorporated into the crystal structure of said compound, whereby the diluted feed solution being tested becomes saturated with said compound by dissolution of a portion of the solid solution in the bed, (3) measuring the concentration of the tracer in the sample after passage through the bed of solid solution, whereby to measure the amount of said compound dissolved from the solid solution to saturate the diluted feed solution, and (4) determining the degree of saturation of said compound in the feed solution from the measured values.

2. A process as defined in claim 1, wherein the solvent is water.

3. A process as defined in claim 1, wherein the compound of limited solubility is gypsum.

4. A process as defined in claim 1, wherein the solvent is water and the compound of limited solubility is gypsum.

5. A process as defined in claim 1, wherein the tracer is chromium in the form of chromate.

6. A process as defined in claim 1, wherein the solid solution is a solid solution of gypsum and chromate.

7. A process as defined in claim 1, wherein said measuring is effected with a spectrophotometer.

* * * * *